US009603722B2

(12) United States Patent
Beverland et al.

(10) Patent No.: US 9,603,722 B2
(45) Date of Patent: Mar. 28, 2017

(54) ALIGNMENT GUIDE

(71) Applicant: DEPUY INTERNATIONAL LIMITED, Leeds (GB)

(72) Inventors: David Beverland, Belfast (IE); Robert Freeman, Halifax (GB); Steven Gowers, Cambridge (GB)

(73) Assignee: DEPUY INTERNATIONAL LIMITED (GB)

( * ) Notice: Subject to any disclaimer, the term of this patent is extended or adjusted under 35 U.S.C. 154(b) by 0 days.

(21) Appl. No.: 14/799,788

(22) Filed: Jul. 15, 2015

(65) Prior Publication Data

US 2015/0313726 A1 Nov. 5, 2015

Related U.S. Application Data

(62) Division of application No. 13/318,483, filed as application No. PCT/GB2010/050710 on Apr. 29, 2010, now Pat. No. 9,114,027.

(30) Foreign Application Priority Data

May 5, 2009 (GB) .................................. 0907650.6

(51) Int. Cl.
*A61F 2/46* (2006.01)
*A61B 17/17* (2006.01)
(Continued)

(52) U.S. Cl.
CPC ............ *A61F 2/4657* (2013.01); *A61B 17/17* (2013.01); *A61B 17/1746* (2013.01);
(Continued)

(58) Field of Classification Search
CPC ........ A61F 2/46; A61F 2/4657; A61F 2/4609; A61B 17/17; A61B 17/1746
See application file for complete search history.

(56) References Cited

U.S. PATENT DOCUMENTS

| 534,434 A | 2/1895 | Frost |
| 1,942,640 A | 1/1934 | Fromme |
| (Continued) | | |

FOREIGN PATENT DOCUMENTS

| CN | 1184409 A | 6/1998 |
| CN | 2647253 Y | 10/2004 |
| (Continued) | | |

OTHER PUBLICATIONS

U.S. Appl. No. 13/318,483—Office Action dated Jan. 15, 2015.
(Continued)

*Primary Examiner* — Christopher Beccia

(57) ABSTRACT

A surgical instrument alignment guide comprising a mount (2) arranged to be coupled to a bone of a patient, an alignment rod (4), a guide rod (24) and an indicator (26). The alignment rod (4) has a first end pivotally coupled to the mount (2) such that the inclination of the alignment rod (4) relative to the mount (2) is adjustable. The guide rod (24) is couplable to a second end of the alignment rod (4) at an adjustable angle and orientation such that the guide rod (24) can extend transverse to the alignment rod (4). The indicator (26) is coupled to the guide rod (24) to indicate when the guide rod (24) lies at a desired angle relative to a horizontal axis. Also disclosed is a method of aligning a surgical instrument using the surgical instrument alignment guide.

6 Claims, 4 Drawing Sheets

(51) Int. Cl.
    *A61F 2/30*      (2006.01)
    *A61B 90/00*     (2016.01)

(52) U.S. Cl.
    CPC ...... *A61F 2/4609* (2013.01); *A61B 2090/068* (2016.02); *A61F 2002/30538* (2013.01); *A61F 2002/4668* (2013.01); *A61F 2002/4687* (2013.01); *A61F 2250/0006* (2013.01)

(56) References Cited

U.S. PATENT DOCUMENTS

| | | | |
|---|---|---|---|
| 2,379,796 | A | 7/1945 | Freeman |
| 4,716,894 | A | 1/1988 | Lazzeri |
| 5,061,270 | A | 10/1991 | Aboczky |
| 5,122,145 | A | 6/1992 | Fishbane |
| D331,461 | S | 12/1992 | Lester |
| 5,250,051 | A | 10/1993 | Maryan |
| 5,284,483 | A | 2/1994 | Johnson |
| 5,320,625 | A | 6/1994 | Bertin |
| 5,364,403 | A | 11/1994 | Petersen |
| 5,457,857 | A | 10/1995 | Lam |
| 5,540,697 | A | 7/1996 | Rehmann |
| 5,584,837 | A | 12/1996 | Petersen |
| 5,658,294 | A | 8/1997 | Sederholm |
| 5,683,399 | A | 11/1997 | Jones |
| 6,395,005 | B1 | 5/2002 | Lovell |
| 6,743,235 | B2 | 6/2004 | Subba Rao |
| 7,037,310 | B2 | 5/2006 | Murphy |
| 8,764,758 | B2 | 7/2014 | Echeverri |
| 9,095,448 | B2 | 8/2015 | Birkbeck |
| 2002/0125756 | A1 | 9/2002 | Asano |
| 2004/0073225 | A1 | 4/2004 | Subba Rao |
| 2004/0152972 | A1 | 8/2004 | Hunter |
| 2005/0107799 | A1 | 5/2005 | Graf |
| 2005/0149054 | A1 | 7/2005 | Gorek |
| 2006/0161167 | A1 | 7/2006 | Myers |
| 2006/0184177 | A1 | 8/2006 | Echeverri |
| 2008/0269757 | A1 | 10/2008 | McMinn |
| 2010/0137871 | A1 | 6/2010 | Borja |
| 2010/0249657 | A1 | 9/2010 | Nycz |
| 2011/0027100 | A1 | 2/2011 | Cummane |
| 2011/0184419 | A1 | 7/2011 | Meridew |
| 2011/0276053 | A1 | 11/2011 | Birkbeck |
| 2012/0330319 | A1 | 12/2012 | Birkbeck |
| 2014/0378984 | A1 | 12/2014 | Birkbeck |

FOREIGN PATENT DOCUMENTS

| | | |
|---|---|---|
| CN | 1689533 A | 11/2005 |
| DE | 10202582 C1 | 9/2003 |
| EP | 1310221 A1 | 5/2003 |
| EP | 1920713 A2 | 5/2008 |
| GB | 2448740 A | 10/2008 |
| JP | 5123335 A | 5/1993 |
| WO | WO 9636284 A1 | 11/1996 |
| WO | WO 9834557 A1 | 8/1998 |
| WO | WO 0130247 A1 | 5/2001 |
| WO | WO 03057087 A2 | 7/2003 |
| WO | WO 2004030556 A2 | 4/2004 |
| WO | WO 2004071360 A2 | 8/2004 |
| WO | WO 2005009303 A1 | 2/2005 |
| WO | WO 2005046475 A1 | 5/2005 |
| WO | WO 2010128320 A1 | 11/2010 |
| WO | WO 2010145769 A1 | 12/2010 |
| WO | WO 2011095804 A1 | 8/2011 |

OTHER PUBLICATIONS

DePuy International Ltd. Pinnacle Acetabular Cup System Surgical Technique; Cat. No. 9068-80-050; Leeds, England, 2003.

DePuy International Ltd. Pinnacle Acetabular Cup System Surgical Technique; Cat. No. 0611-42-050 (Rev. 3); Aug. 24, 2004; USA.

DePuy International Ltd. Pinnacle Acetabular Cup System Surgical Technique; Cat. No. 9068-80-050 version 2; Jun. 2009; Leeds, England.

Langston, D.J., et al.; The Effect of Component Size and Orientation on the Concentrations of Metal Ions After Resurfacing Arthroplasty of the Hip; The Journal of Bone & Joint Surgery, pp. 1143-1152, vol. 90-B, No. 9, Sep. 2008, England.

Murray, D.W.; The Definition and Measurement of Acetabular Orientation; the Journal of Bone and Joint Surgery, pp. 228-232, vol. 75•B, No. 2, Mar. 1993, England.

L. Fabeck, et al., "A Method to Measure Acetabular Cup Anteversion After Total Hip Replacement,", Acta Orthopaedica Belgica. vol. 65- 4- 1999, 485-491.

Pinnacle Acetabular Cup System, Surgical Technique; 2002, 49 pages, DePuy Orthopaedics, Inc.

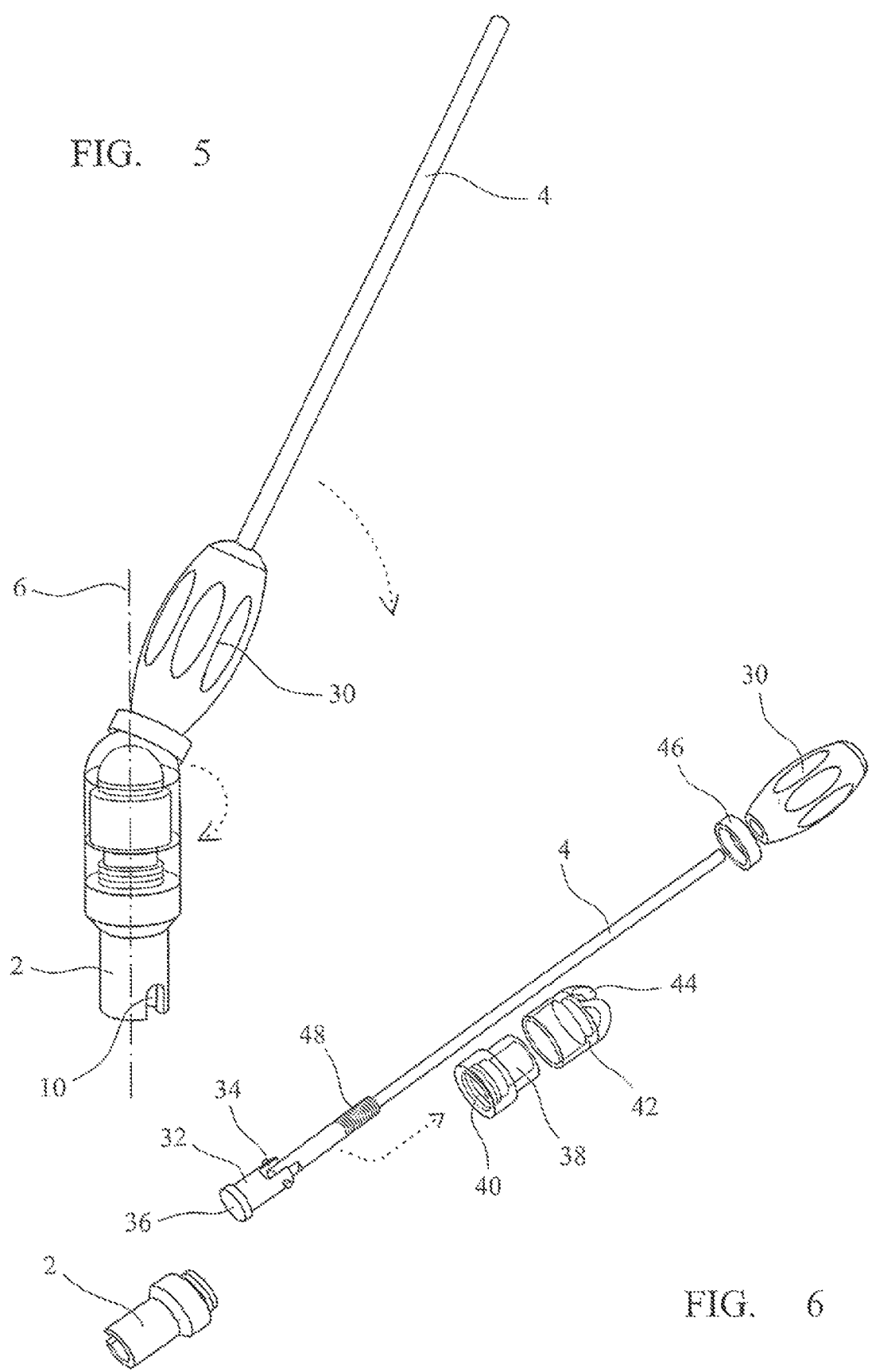

ALIGNMENT GUIDE

CROSS REFERENCE TO RELATED APPLICATION

The present application is a divisional of U.S. application Ser. No. 13/318,483 filed Apr. 29, 2010, which is a National Stage 35 U.S.C. 371 of International Patent Application PCT/GB2010/050710 filed Apr. 29, 2010, claiming priority to United Kingdom Application No. GB 0907650.6 (now abandoned), both of which are incorporated by reference in their entireties.

The present invention relates to an alignment guide. In particular, the present invention relates to an alignment guide for aligning an instrument, more particularly a surgical instrument.

During surgical procedures it is commonly necessary to accurately locate prostheses and instruments. For instance, during implantation of an acetabular cup into a pelvis, it is important to ensure that the cup is accurately located within a reamed cavity. Typically, such a procedure requires a number of separate instruments to be used. It is important to ensure that the alignment determined for the cup during initial surgical steps is maintained during later surgical steps. For instance, position of the cup may be initially determined. The cavity must then be reamed. It is important that the desired version angle and inclination (that is, the varus-valgus angle) of the cup is maintained during the reaming by ensuring that the reamer is aligned correctly relative to the instruments used to determine the initial position of the cup to ensure that the cavity is correctly located. Additionally, it is important to either detect that the patient's pelvis has moved during the surgical procedure, or to ensure that the alignment of the acetabular cup has also shifted by a corresponding amount.

Inclination and version guides are widely used during total hip arthroplasty to assist in aligning the acetabular cup. Separate guides may be provided for inclination and version angle. Alternatively, a combined guide may be provided. One known form of combined alignment guide enables the position of the acetabular cup to be set at an angle relative to the floor of the operating room and the long axis of the patient. However, such an alignment takes no account of movement of the patient on the operating table during surgery. Regardless of changes in the patient's position, the alignment guide indicates the same orientation of the acetabular cup. Consequently, either the patient must be maintained in a strictly lateral position or the surgeon must be alert to spotting changes in the desired cup position caused by the patient moving.

An alternative acetabular cup alignment guide, which is commercially available from San-Tech Surgical Sàrl and described in PCT publication WO-2005/009303, uses a pair of spirit levels. A first spirit level is coupled to the patient's pelvis to indicate if the patient's position has changed. A second spirit level is coupled to the surgical instrument. Changes in inclination of the instrument can be detected by a shift within the second spirit level. Changes in the version angle are detected by referring to the relative position of the first spirit level and a wire arm which extends from the second spirit level. Whilst offering improved accuracy, such an alignment guide is relative difficult to use as it comprises multiple separate components and requires multiple measurement steps.

It is an object of embodiments of the present invention to obviate or mitigate one or more of the problems associated with the prior art, whether identified herein or elsewhere.

According to a first aspect of the present invention there is provided a surgical instrument alignment guide comprising: a mount arranged to be coupled to a bone of a patient; an alignment rod having a first end pivotally coupled to the mount such that the inclination of the alignment rod relative to the mount is adjustable; a guide rod couplable to a second end of the alignment rod at an adjustable angle and orientation such that the guide rod can extend transverse to the alignment rod; and an indicator coupled to the guide rod to indicate when the guide rod lies at a desired angle relative to a horizontal axis.

An advantage of the first aspect of the present invention is that the alignment guide may be used to indicate a desired alignment of a prosthetic implant such as an acetabular cup. The position information, in particular the required varus-valgus angle and the version angle, is then preserved during the surgical procedure, even in the event that the patient's position on the operating table changes. Furthermore the alignment guide can be positioned and set prior to dislocating the patient's joint so that the alignment can be set to the patient's natural anatomy. The alignment guide assists the surgeon in visualising the required angles at each stage of the surgical procedure.

The mount may comprise a bore arranged to receive a guide pin protruding from the bone.

The alignment rod may be arranged to pivot relative to the mount in any direction about a mount axis which passes through the pivot point into the bone. The angle subtended between the mount axis and the alignment rod may be adjustable between 0° and 60°.

The first end of the alignment rod may comprise a partially spherical portion and the mount may comprise a corresponding concave surface arranged to receive the partially spherical portion.

The surgical instrument alignment guide may further comprise a locking sleeve disposed about the mount having an internal screw thread arranged to mate with an exterior screw thread on the surface of the mount, the locking sleeve further comprising an aperture through which the alignment rod extends the aperture having a diameter smaller than that of the partially spherical portion such that the partially spherical portion is arranged to bear against the concave surface of the mount when the locking sleeve is rotated in a first direction relative to the mount.

The surgical instrument alignment guide may further comprise an intermediate component rotatably coupled to the mount and coupled to the alignment rod via a hinge.

The surgical instrument alignment guide may further comprise a sleeve positioned over the intermediate component, the sleeve having an elongate slot through which the alignment rod can pivot and a locking sleeve disposed about the alignment rod, the locking sleeve having an internal screw thread arranged to mate with an exterior screw thread on the surface of the alignment rod, the locking sleeve being arranged to bear against the sleeve about the intermediate component when the locking sleeve is rotated in a first direction relative to the alignment rod.

The indicator may comprise a spirit level coupled to the guide rod to indicate when the guide rod lies in a horizontal plane.

According to a second aspect of the present invention there is provided a method of aligning a surgical instrument, the method comprising: inserting a guide pin into a bone of a patient such that the guide pin protrudes from the bone; coupling a surgical instrument alignment guide to the guide pin, the alignment guide comprising a mount having a bore arranged to receive the protruding portion of the guide pin and an alignment rod having a first end pivotally coupled to the mount; coupling a guide rod to a second end of the alignment rod; adjusting the angle and orientation of the guide rod relative to the alignment rod until it is at a predetermined angle and orientation and the guide rod extends transverse to the alignment rod; adjusting the inclination and orientation of the alignment rod relative to the mount until the alignment rod extends from the bone such that it indicates a desired instrument orientation relative to the bone, the guide rod extends at a predetermined angle relative to a long axis of the patient and an indicator coupled to the guide rod indicates that the guide rod lies at a desired angle relative to a horizontal axis; and aligning a surgical instrument such that a longitudinal instrument axis is parallel to the alignment rod.

The method may further comprise coupling a guide rod to a second end of the alignment rod at a predetermined angle and orientation and manipulating the alignment rod and the guide rod until the guide rod is aligned with a long axis of the patient.

Adjusting the inclination of the alignment rod relative to the mount may comprise adjusting the inclination of the alignment rod relative to the mount until a spirit level coupled to the guide rod lies in a horizontal plane.

The method may further comprise locking the inclination of the alignment rod relative to the mount.

The present invention will now be described, by way of example only, with reference to the accompanying drawings, in which:

FIG. 5 illustrates a surgical instrument alignment guide in accordance with a second embodiment of the present invention; and FIG. 6 is an exploded view of the surgical instrument alignment guide of FIG. 5.

Figure 1:
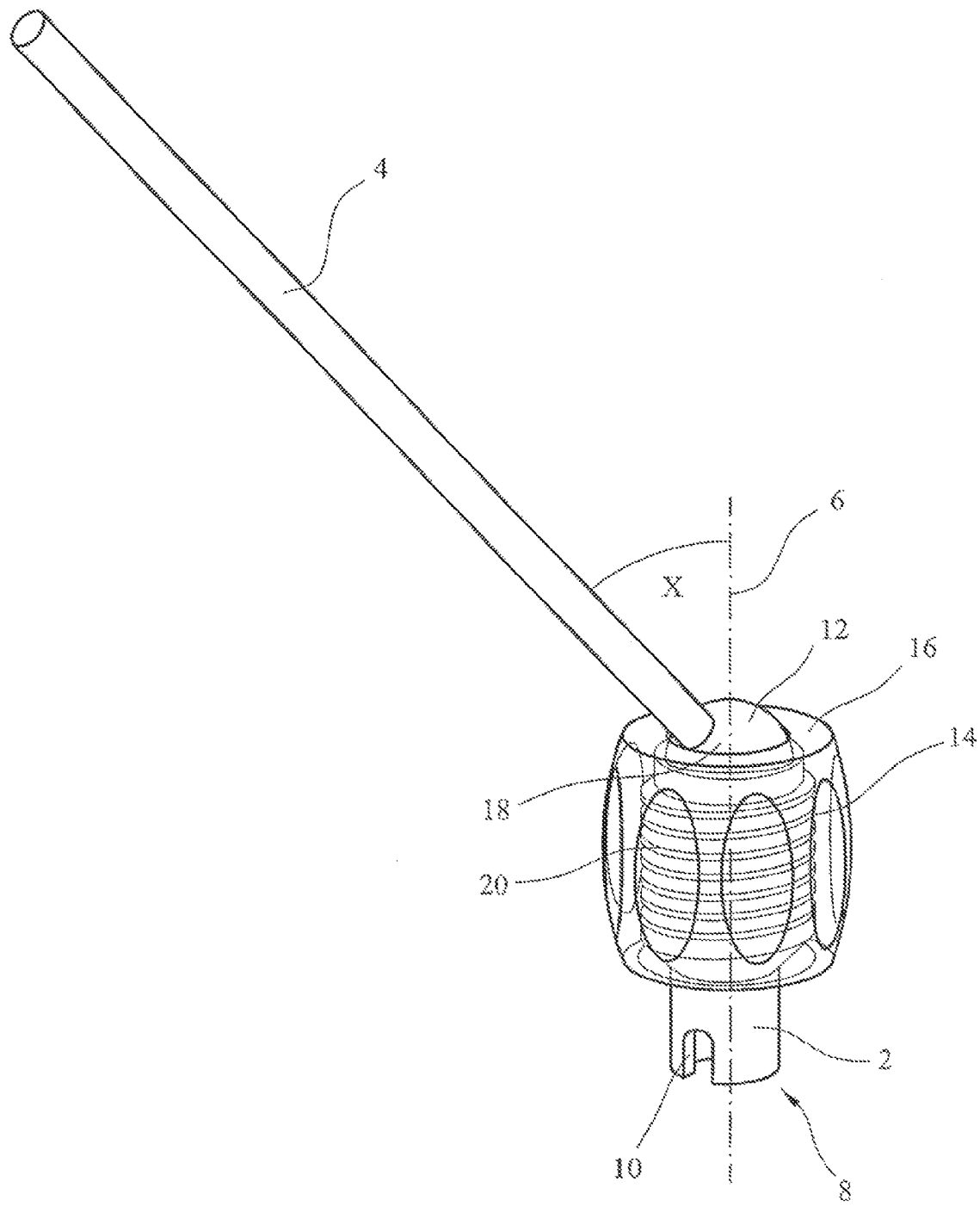
FIG. 1 illustrates a surgical instrument alignment guide in accordance with a first embodiment of the present invention.

Referring first to FIG. 1, this schematically illustrates an alignment guide in accordance with a first embodiment of the present invention. Portions of the alignment guide are illustrated as being partially transparent in order to illustrate underlying features. The alignment guide is suitable for use during a surgical procedure for recording and preserving alignment information for a prosthetic implant such as a prosthetic acetabular cup. The alignment guide assists with correctly aligning surgical instruments during the implantation procedure. Advantageously, this helps to reduce misalignment of the implant and therefore helps to minimise wear of the implant.

The alignment guide comprises a mount 2 which is arranged to be coupled to a bone of a patient and an alignment rod 4. The alignment rod 4 has a first end coupled to the mount 2 such that the inclination of the alignment rod 4 relative to an axis 6 extending through the mount 2 is adjustable.

Mount 2 comprises a bore 8 extending into the underside of the mount 2. Bore 8 is arranged to receive a guide pin extending from a bone of a patient. For instance, when the alignment guide is used to align an acetabular cup, the guide pin is inserted into the patient's pelvis spaced apart from the implant location. The guide pin may in particular be a Charnley pin. The guide pin is preferably not circular in cross section, with bore 8 having a corresponding cross section, such that the mount 2 does not rotate relative to the guide pin. For instance, the guide pin may be generally cylindrical with a laterally projecting tab. The bore 8 includes a cut out 10 corresponding to the tab such that the guide pin may only be received within the bore 8 in a single angular position. Advantageously, the alignment guide may thus be removed from the guide pin and then replaced in the same angular position. It will be appreciated by the appropriately skilled person that the mount may be temporarily secured to the bone in other ways, for instance using an adhesive.

The first end of the alignment rod 4 comprises a partially spherical portion 12. An upper surface of the mount 4 comprises a corresponding concave surface (not visible in FIG. 1). The arrangement is such that alignment rod 4 can pivot relative to the mount 2 about a pivot located at the centre of the partially spherical portion 12. Mount axis 6 extends through the pivot point between the mount 2 and the rod 4. The alignment rod 4 can be manipulated such that it can pivot in any direction about the mount axis 6. The inclination of the alignment rod 4 relative to the mount axis 6 is indicated by angle x. The inclination may vary between 0° and 60°. A relatively large range of inclination is required to ensure that regardless of the position of the mount 2 upon the surface of the pelvis, and regardless of the surgical approach used to expose the pelvis, the alignment rod 4 may be positioned such that it extends parallel to a chosen implantation axis for the acetabular cup.

Mount 2 is generally cylindrical and further comprises an exterior screw thread 14 located about mount axis 6. The alignment guide further comprises a locking sleeve 16 which fits over the partially spherical portion 12 and the mount 2. The locking sleeve 16 comprises a narrowed aperture 18 at a first end through which the alignment rod 4 extends. The locking sleeve 16 further comprises an interior screw thread 20 which is arranged to mate with the exterior screw thread 14 on the mount 2. Tightening the locking sleeve 16 over the mount 2 by rotating the locking sleeve 16 relative to the mount 2 causes the edges of aperture 18 to bear against the partial sphere 12, which in turn bears against the concave mount surface, locking the inclination of the alignment rod 4 relative to the mount axis 6 and locking the direction in which the alignment rod 4 extends from the mount 2.

The alignment guide of FIG. 1 may be used during a surgical procedure to implant an acetabular cup to ensure that the cup is implanted at a chosen inclination (varus-valgus angle) and at a chosen version angle. The same alignment guide may be used regardless of the surgical approach used. A guide pin is inserted into an exposed portion of the patient's pelvis such that it protrudes from the bone. The guide pin may be positioned at any convenient location spaced apart from the acetabulum such that the alignment guide will not interfere with the preparation of the acetabulum. The alignment guide is positioned over the guide pin such that the pin is received within bore 8. If a guide pin with a non-circular cross section is used then the mount will only couple to the pin in a single angular position, as described above.

The surgeon may then set the orientation of the alignment rod 4 such that the alignment rod 4 extends parallel to a required axis of the acetabular cup. This orientation of the alignment rod 4 may be performed manually with reference to the patient's anatomy, that is by alignment to local reference features of the pelvis. In particular, the orientation of the alignment rod 4 may be determined relative to local acetabular landmarks for the natural pelvis before they are reamed away. Additionally, the inclination may be determined with reference to the natural joint before the femoral head is dislocated. When the alignment rod is orientated in this way, the alignment can be considered to have been performed with respect to the required local varus-valgus and version angles.

Alternatively, the orientation of the alignment rod 4 may be performed relative to global angles, that is with respect to a global coordinate system based upon the patient's long axis and the horizontal plane. For such an alignment technique, it is desirable to ensure that the patient is accurately positioned upon the operating table with the patient's pelvis correctly positioned in a predetermined orientation to ensure that the global angles correspond to the local angles relative to the pelvis. If the patient is correctly positioned upon the operating table then orientating the alignment rod with respect to the global varus-valgus and version angles can be easier and more accurate and requires less of the pelvis to be visible to the surgeon.

Once the required inclination has been determined, the locking sleeve 16 is tightened to secure the alignment rod in position. During the preparation of the bone and the implantation of the cup, the same alignment is preserved by ensuring that the surgical instruments, and in particular the cup introducer, are positioned parallel to or at a predetermined angle with respect to the alignment rod 4. As the inclination of the alignment rod 4 is set relative to the guide pin, the alignment guide may be temporarily removed during portions of the surgical procedure and then later replaced without losing reference to the initial cup position. Furthermore, even if the patient moves upon the operating table, as the alignment guide is directly coupled to the pelvis, the required alignment is preserved.

Figure 2:
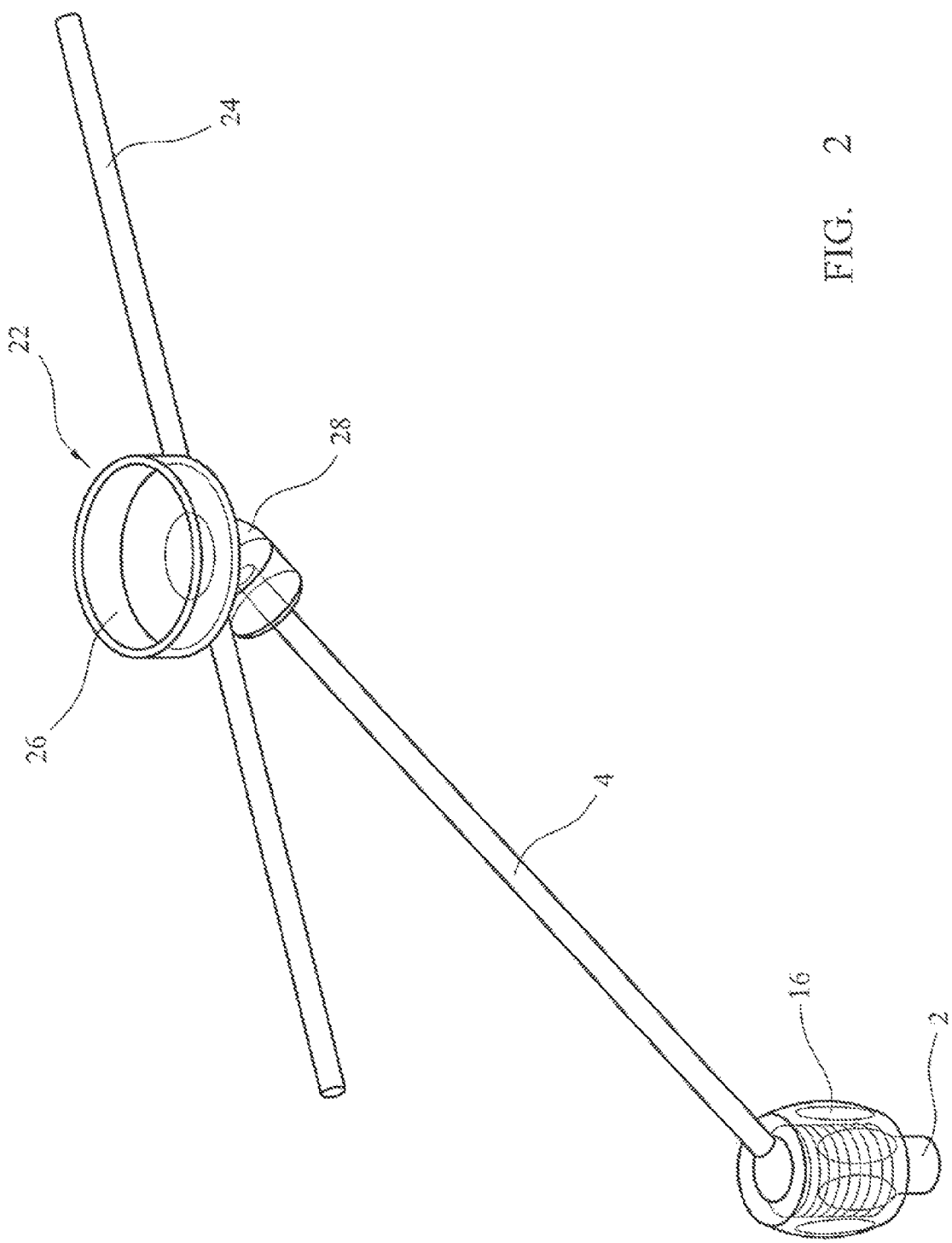
FIGS. 2 to 4 illustrate the alignment guide of FIG. 1 further including a version angle guide.

Referring now to FIG. 2, this illustrates the alignment guide of FIG. 1 further incorporating a slip on version angle guide 22. The version angle guide 22 comprises a version angle rod 24 and a spirit level 26. The version angle guide 22 couples to the free end of the alignment rod 4 via joint 28. Joint 28 couples the version angle rod 24 to the alignment rod at fixed angle and orientation. However, in accordance with other embodiments of the present invention, the joint 28 may allow the angle and orientation to be varied, for instance between discrete angular intervals.

The version angle guide 24 assists in orientating the alignment rod 4 when the alignment is to be performed relative to the global varus-valgus and version angles. Once the patient is correctly positioned upon the operating table, the guide pin is inserted into the patient's pelvis and the mount 2 secured to the guide pin as described above. However, before locking sleeve 16 is tightened, the slip on version angle guide 22 is coupled to the end of the alignment rod 4. The version angle rod 24 and the alignment rod 4 may then be manipulated together until the version angle rod 24 is aligned with the patient's long axis and lies within a horizontal plane, as determined by the spirit level 26. The spirit level 26 may comprise a bulls-eye spirit level, as shown, for positioning the version angle rod 24 in the horizontal plane. Alternatively, two linear spirit levels extending along orthogonal axes may be provided to achieve the same position of the version angle rod 24 within the horizontal plane. As a further alternative, the spirit level 26 may be replaced with a plumb line or fixed rod to be aligned with the a vertical axis to ensure that the version angle rod 24 lies in a horizontal plane.

As the version angle rod 24 is coupled to the alignment rod 4 at a known angle and orientation, and as the spirit level 26 is securely fixed to the version angle rod 24, positioning the alignment guide with respect to the horizontal plane and the patient's long axis in this way ensures that the alignment rod 4 is aligned parallel to the required implantation axis for the acetabular cup. Once the alignment rod 4 has been correctly orientated, the locking sleeve 16 is tightened to secure the alignment rod 4 to the mount 2. The version angle guide 22 may then be removed from the alignment guide, if required, to provide more space for the surgeon to operate.

Figure 3:
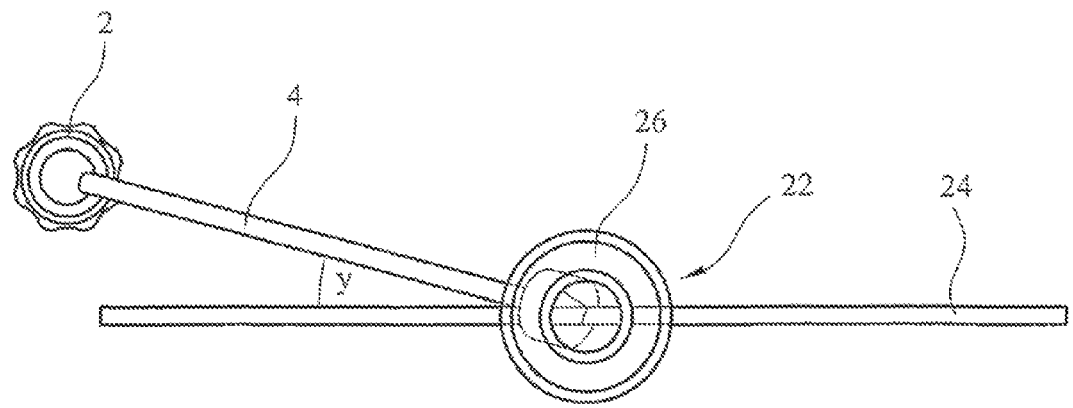
Figure 4:
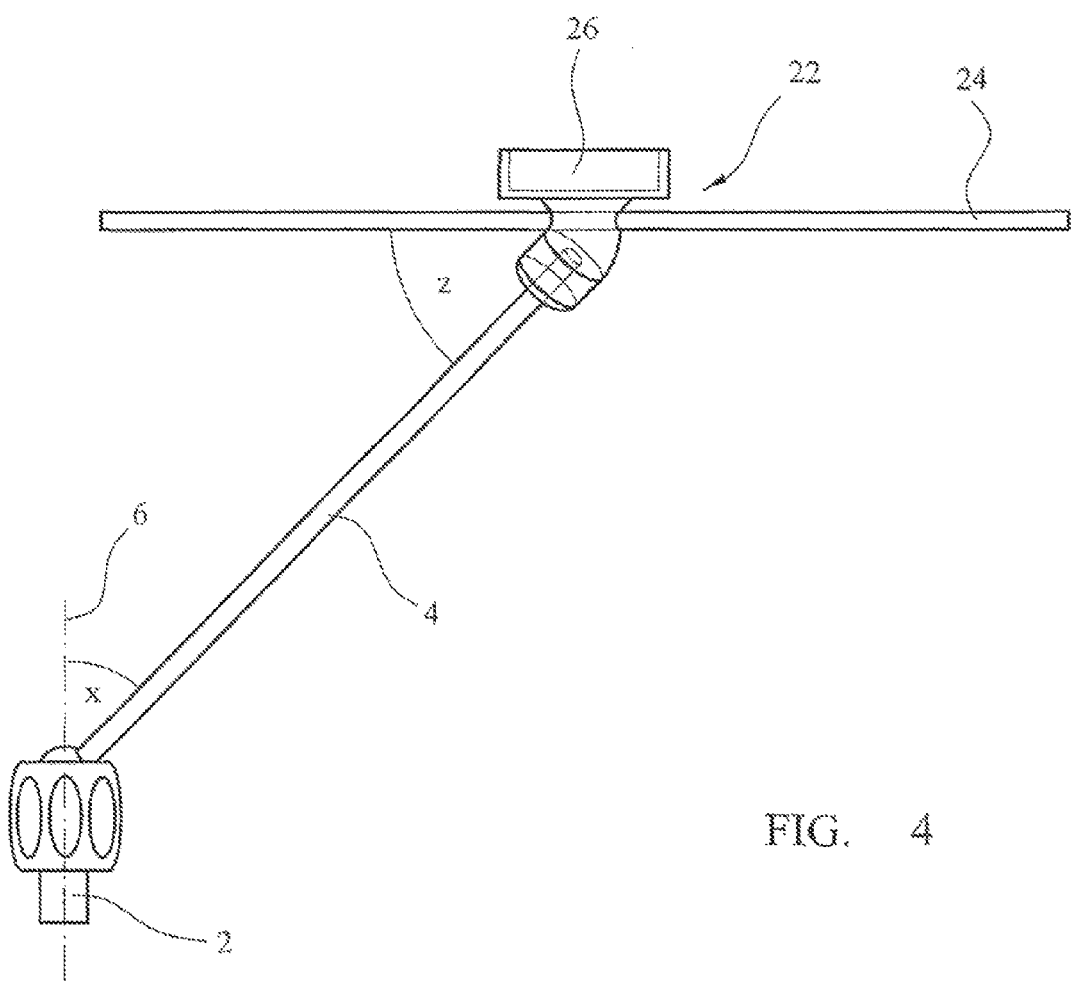

FIGS. 3 and 4 illustrate the alignment guide with the slip on version angle guide 22 of FIG. 2 in a plan view and a side view respectively. The version angle guide 22 allows the surgeon to reference global angles prior to dislocation of the hip, that is the surgeon is able to orientate the alignment rod 4 with respect to the patient's long axis and a horizontal plane in order to achieve the desired varus-valgus and version angles. Advantageously, the surgeon has the best knowledge of the patient's orientation on the operating table prior to dislocating the hip joint and so the alignment guide may be adjusted more accurately.

FIG. 3 shows a plan view of the alignment guide. As discussed above, the version angle rod 24 may be secured to the alignment rod 4 at a fixed angle and orientation. However, in alternative embodiments of the present invention, joint 28 may be adjustable to allow the surgeon to vary to varus-valgus and version angles. As a further alternative, a range of slip on version guides 22 at varying varus-valgus and version angles may be provided. Angle y is the angle subtended between the alignment rod 4 and the version angle rod 24. Angle y is equal to the version angle when the version angle rod 24 is aligned with the patient's long axis and positioned in a horizontal plane. The version angle y may equal 15°. Alternatively, the version angle may be variable between 0° and 30°. FIG. 3 illustrates a slip on version guide 22 for use in positioning an acetabular cup for a left hip. It will be appreciated that in order to correctly align an acetabular cup for a right hip, a mirror image version guide 22 must be used in which the version angle rod 24 is rotated clockwise to form the same angle y with the alignment rod 4. Alternatively, a single version angle guide 22 may be provided in which joint 28 is rotatable to allow angle y to be inverted such that the same guide may be used for left and right hips.

FIG. 4 shows a side view of the alignment guide. Angle z is the angle subtended between the alignment rod 4 and the version angle rod 24. Angle z is equal to the required varus-valgus angle (if the pelvis remains correctly positioned upon the operating table). Angle z may be fixed at 45° or may be variable. Angle x is not directly related to the varus-valgus angle or to the version angle as angle x is dependent upon the orientation of the guide pin protruding from the bone relative to the required acetabular cup implantation axis.

Referring now to FIG. 5, this illustrates an alignment guide in accordance with a second embodiment of the present invention. Portions of the alignment guide of FIG. 5 that are equivalent to the alignment guide of FIG. 1 are indicated by the same reference numbers. The alignment guide of FIG. 5 may be used in combination with the same version angle guide 22 shown in FIGS. 2 to 4. The alignment guide of FIG. 5 differs from that of FIG. 1 in the coupling between the mount 2 and the alignment rod 4, and also in the locking mechanism. Specifically, a locking sleeve 30 is provided positioned about the alignment rod 4 instead of around the mount 2, which allows the alignment guide to be positioned and locked using a single hand. This allows the surgeon to have a free hand to control another surgical instrument.

FIG. 6 is an exploded view of the alignment guide of FIG. 5, which better illustrates the coupling and locking mechanisms. Mount 2 is coupled to the alignment rod 4 via an intermediate component 32. Intermediate component 32 is connected to the alignment rod 4 via a hinge 34. Intermediate component 32 further comprises a circular base plate 36 which is received within a corresponding circular socket within the mount 2 (not visible in FIG. 6). The intermediate component 32 may therefore rotate relative to the mount 2. This rotary movement, in combination with the hinged connection to the alignment rod 4, provides the same range of movement as for the partially spherical portion 12 and concave mount surface for the alignment guide of FIG. 1.

The intermediate component 32 is secured to the mount 2 by a locking sleeve 38 which includes a bore 40 to receive the intermediate component 32, which can rotate within bore 40. Bore 40 incorporates an internal thread which mates with an external thread provided upon mount 2 to couple the mount 2 and the locking sleeve 38 together. A further sleeve 42 is seated over the locking sleeve 38. Sleeve 42 incorporates a slot 44 through which the alignment rod 4 extends and pivots. Sleeve 42 is arranged to rotate with the intermediate component 32 such that slot 44 remains aligned with the plane within which the alignment rod 4 pivots.

The locking mechanism for the alignment guide of FIGS. 5 and 6 comprises a locking sleeve 30 and a washer 46. Locking sleeve 30 incorporates an internal thread which mates with external thread 48 provided on alignment rod 4. Rotating locking sleeve 30 about the alignment rod 4 causes the washer 46 to bear against sleeve 42 and prevents alignment rod 4 from pivoting through slot 44. Furthermore, sleeve 42 in turn bears against locking sleeve 38 preventing relative movement between the two sleeves, and hence preventing the alignment rod 4 from rotating relative to mount 4.

In alternative embodiments of the present invention, in place of the version angle guide 22 incorporating a version angle rod 24, a laser pointer may be coupled to the alignment rod at a predetermined angle and orientation such that a beam of light may be projected and aligned with the patient's long axis.

Embodiments of the present invention have been described above primarily with reference to using the alignment guide during a surgical procedure to implant an acetabular cup. However, the present invention is not limited to this application of the alignment guide. The alignment guide may be coupled to any bone in order to preserve alignment information. For instance, the alignment guide may be coupled to the scapula during surgery upon the shoulder joint.

Further modifications to, and applications of, the present invention will be readily apparent to the skilled person from the teaching herein, without departing from the scope of the appended claims.

The invention claimed is:

1. A method of aligning a surgical instrument, the method comprising the steps of:

inserting a guide pin into a bone of a patient such that the guide pin protrudes from the bone;

coupling a surgical instrument alignment guide to the guide pin, the alignment guide comprising a mount having a bore arranged to receive the protruding portion of the guide pin and an alignment rod having a first end pivotally coupled to the mount;

coupling a guide rod to a second end of the alignment rod such that the guide rod extends transverse to the alignment rod;

adjusting the inclination and orientation of the alignment rod relative to the mount until the alignment rod extends from the bone such that the alignment rod indicates a desired instrument orientation relative to the bone, the guide rod extends at a predetermined angle relative to a long axis of the patient, and an indicator coupled to the guide rod indicates that the guide rod lies at a desired angle relative to a horizontal axis; and aligning a surgical instrument such that a longitudinal instrument axis is parallel to the alignment rod.

2. The method of claim 1, wherein the step of adjusting the inclination and orientation of the alignment rod relative to the mount comprises adjusting the alignment rod relative to the mount until the indicator indicates that guide rod lies in a horizontal plane.

3. The method of claim 1, further comprising the step of locking the alignment rod relative to the mount.

4. The method of claim 1, wherein the step of locking the alignment rod includes using a locking sleeve disposed about the mount, the locking sleeve having an internal screw thread arranged to mate with an exterior screw thread on the surface of the mount, the locking sleeve having an aperture through which the alignment rod extends, the aperture having a diameter smaller than that of the partially spherical portion such that the partially spherical portion is arranged to bear against the concave surface of the mount when the locking sleeve is rotated in a first direction relative to the mount.

5. The method of claim 1, wherein the alignment rod is pivotable between 0° and 60°.

6. The method of claim 1, wherein the indicator comprises a spirit level coupled to the guide rod to indicate when the guide rod lies in a horizontal plane.

* * * * *